US007932253B2

(12) United States Patent
Matthews

(10) Patent No.: US 7,932,253 B2
(45) Date of Patent: Apr. 26, 2011

(54) IMMUNOMODULATING OXOPYRRAZOLOCINNOLINES AS CD80 INHIBITORS

(75) Inventor: Ian Richard Matthews, Abingdon (GB)

(73) Assignee: MediGene AG, Martinsried (DE)

( * ) Notice: Subject to any disclaimer, the term of this patent is extended or adjusted under 35 U.S.C. 154(b) by 379 days.

(21) Appl. No.: 11/659,035

(22) PCT Filed: Aug. 9, 2004

(86) PCT No.: PCT/GB2004/003422
§ 371 (c)(1),
(2), (4) Date: Oct. 27, 2008

(87) PCT Pub. No.: WO2006/016093
PCT Pub. Date: Feb. 16, 2006

(65) Prior Publication Data
US 2009/0062289 A1 Mar. 5, 2009

(51) Int. Cl.
C07D 487/04 (2006.01)
A61K 31/5025 (2006.01)
A61P 19/02 (2006.01)
A61P 9/10 (2006.01)
A61P 7/12 (2006.01)
A61P 11/06 (2006.01)
A61P 17/06 (2006.01)

(52) U.S. Cl. ........................ 514/248; 544/234
(58) Field of Classification Search .................. 544/234; 514/248
See application file for complete search history.

(56) References Cited

U.S. PATENT DOCUMENTS

| 3,576,637 | A | 4/1971 | Suga et al. |
| 4,591,589 | A | 5/1986 | Gasc et al. |
| 5,061,705 | A | 10/1991 | Wuest et al. |
| 7,276,505 | B2 * | 10/2007 | Matthews ................. 514/248 |
| 7,566,713 | B2 | 7/2009 | Mathews |
| 7,598,247 | B2 | 10/2009 | Matthews |
| 2007/0213345 | A1 | 9/2007 | Matthews |
| 2009/0062289 | A1 | 3/2009 | Matthews |
| 2009/0221590 | A1 | 9/2009 | Matthews |
| 2009/0312334 | A1 | 12/2009 | Matthews |

FOREIGN PATENT DOCUMENTS

| EP | 0255892 | 2/1988 |
| EP | 0269030 | 6/1988 |
| GB | 629412 | 9/1949 |
| WO | 97/34893 | 9/1997 |
| WO | 99/00391 | 1/1999 |
| WO | 03/004485 | 1/2003 |
| WO | WO 03/004495 A | 1/2003 |
| WO | 2004/048378 | 6/2004 |
| WO | 2004/055014 | 7/2004 |
| WO | WO 2004/081011 | 9/2004 |
| WO | WO 2004/081011 A | 9/2004 |
| WO | WO 2005/116033 | 12/2005 |
| WO | WO 2007/096588 | 8/2007 |

OTHER PUBLICATIONS

Griesser, Ch. 8, The Importance of Solvates (pp. 211-230), in the text, Polymorphism: In the Pharmaceutical Industry, Hilfiker, 2006.*
Brittain, Chapter V of Polymorphism in Pharmaceutical Solids, 1999, pp. 126-127.*
MediGene, http://www.medigene.de/englisch/ProjektRH.php, downloaded Aug. 28, 2009.*
ClinicalTrials.gov, http://clinicaltrials.gov/ct2/show/NCT00704119, last updated Nov. 4, 2008, downloaded Mar. 10, 2010.*
D.E. Ames et al: "Preparation of cinnoline-3,4-dicarbonitrile and -dicarboxylic acid", Tetrahedron, vol. 37, No. 14, 1981, pp. 2489-2491, XP002333094.
Appel & Brossart, "Development of Novel Compounds to Treat Autoimmune and Inflammatory Diseases and Graft Versus Host Reactions," Endocrin. Metab. Immune Disord. Drug Targets 7, 93-97, 2007.
Brumeanu et al., "Down-regulation of autoreactive T-cells by HMG CoA reductase inhibitors," Clin. Immunol. 119, 1-12, 2006.
Chitale and Moots, "Abatacept: the first T lymphocyte co-stimulation modulator, for the treatment of rheumatoid arthritis," Expert. Opin. Biol. Ther. 2008; 8:115-122.
Choy, "T Cells in Psoriatic Arthritis," Curr. Rheumatol. Rep. 6, 437-41, 2007.
Cope et al., "The central role of T cells in rheumatoid arthritis," Clin. Exp. Rheumatol. 24, 4-11, 2007.
Dubey et al., "Costimulatory requirements of naive CD4+ T cells. ICAM-1 or B7-1 can costimulate Naïve CD4 T Cell Activation but Both Are Required for Optimum Response," J Immunol.1995; 155: 45-57.
Gimmi et al., "Human T-cell clonal anergy is induced by antigen presentation in the absence of B7 costimulation," Proc. Nat. Acad. Sci. USA 90, pp. 6586-6590, Jul. 1993.
Kobata et al., "Role of costimulatory molecules in autoimmunity," Rev. Immunogenet. 2, 74-80, 2000.
Kristensen et al., "The number needed to treat for adalimumab, etanercept, and infliximab based on ACR50 response in three randomized controlled trials on established rheumatoid arthritis: a systematic literature review," Scand. J. Rheumatol. 2007; 36:411-417.
Linsley et al., "Binding of the B Cell Activation Antigen B7 to CD28 Costimulates T Cell Proliferation and Interleukin 2 mRNA Accumulation," J. Exp. Med. 173, 721-30, Mar. 1991.
Mallone & Endert, "T Cells in the Pathogenesis of Type 1 Diabetes," Curr. Diab. Rep. 8, 101-06, 2008.
Suresh et al., "Role of CD28-B7 Interactions in Generation and Maintenance of CD8 T Cell Memory," The Journal of Immunology, 2001, 167: 5565-5573.
Weiss et al., ."Role of CD28-B7 Interactions in Generation and Maintenance of CD8 T Cell Memory," Neuroimmunol. 191, 79-85, 2007.

(Continued)

Primary Examiner — James O Wilson
Assistant Examiner — Cecilia M Jaisle
(74) Attorney, Agent, or Firm — Banner & Witcoff, Ltd.

(57) ABSTRACT

N-(1-Aza-bicyclo[2.2.2]oct-3-yl)-4-(6,9-difluoro-3-oxo-1,3-dihydro-pyrazolo[4,3-c]cinnolin-2-yl)-benzamide is a CD80 antagonist, useful in the treatment of diseases which benefit from immuno-inhibition.

4 Claims, No Drawings

OTHER PUBLICATIONS

Medigene Press Release, "RhuDex(TM) Clinical Development to Continue Following Feedback from Regulatory Authorities," Oct. 5, 2009.

Collins et al., "The interaction properties of costimulatory molecules revisited," *Immunity*, vol. 17, pp. 201-210, 2002.

Lenschow et al., "CD28/B7 system of T cell costimulation,"*Annu. Rev. Immunol.*, vol. 14, pp. 233-258, 1996.

Byun et al., "Preparation of polymer-bound pyrazoloneactive esters for combinatorial chemistry," Tetrahedron Letters, vol. 44, pp. 8063-8067, Oct. 2003.

Huxley et al., "High-affinity small molecule inhibitors of T cell costimulation," Chem. Biol., vol. 11, pp. 1651-1658, 2004.

Lukes et al., "Oral feeding with pig peripheral lymphocytes decreases the xenogeneic delayed type hypersensitivity reaction in galactosyltransferase knockout mice," Abstract, Transplant Proc., vol. 37, No. 8, pp. 3327-3331, 2005.

Ninomiya et al., "Phosphorus in Organic Synthesis—VII," Tetrahedron, vol. 30, No. 4, pp. 2151-2157, 1974.

Salomon et al., B7/CD28 costimulation is essential for the homeostasis of the CD4+CD25+ immunoregulatory T cells that control autoimmune diabetes; Immunity, vol. 12, pp. 431-440, 2000.

Saxena et al., "Abrogation of DTH response and mitogenic lectin- and alloantigen-induced activation of lymphocytes by calcium inhibitors TMB-8 and BAPTA-AM," Immunol. Lett., vol. 101, No. 1, pp. 60-64, Oct. 15, 2005.

Strieth et al., "Paclitaxel encapsulated in cationic liposomes increases tumor microvessel leakiness and improves therapeutic efficacy in combination with Cisplatin," Clin Cancer Res., vol. 14, No. 14, pp. 4603-4611, 2008.

Strieth et al., "Tumor-selective vessel occlusions by platelets after vascular targeting chemotherapy using paclitaxel encapsulated in cationic liposomes," Int J Cancer, vol. 122, No. 2, pp. 452-460, 2008.

Weiss et al., "CD8+ T cells in inflammatory demyelinating disease," J Neuroimmunol., vol. 191, Nos. 1-2, pp. 79-85, Nov. 2007.

West, "Solid state chemistry and its applications," Wiley & Sons, New York, book Chapter 10, pp. 358-359, 1988.

Heller, "Zur Kenntnis der Arylamide aromatischer Carbon- und Sulfosäuren," J. Prakt. Chemie 121, 193-203, 1929.

Michaelis, "Über die Anhydride der 1-Phenyl-5- und -3-pyrazolon-o-carbonsäuren," 129-212, Justus Liebigs Annalen der Chemie 373, 129-238, 1910.

Picciola et al., "Composti Eterociclici a Potenziale Attivita Antiinflammatoria Contenenti II Residuo di un Acido 4-Amminofenilalcanoico," Il Farmaco 39, 371-378, 1984 (English abstract).

* cited by examiner

IMMUNOMODULATING OXOPYRRAZOLOCINNOLINES AS CD80 INHIBITORS

CROSS REFERENCE TO RELATED APPLICATIONS

This application is a National Stage application of co-pending PCT application PCT/GB2004/003422 filed Aug. 9, 2004. This application is incorporated herein by reference in its entirety.

The present invention relates to the immunoinhibitory CD80 antagonist compound N-(1-aza-bicyclo[2.2.2]oct-3-yl)-4-(6,9-difluoro-3-oxo-1,3-dihydro-pyrazolo[4,3-c]cinnolin-2-yl)-benzamide, to a method for its preparation, to compositions containing it, and to its for clinical treatment of medical conditions which benefit from immunomodulation, e.g. autoimmune disease, rheumatoid arthritis, multiple sclerosis, diabetes, asthma, transplantation, systemic lupus erythematosis and psoriasis.

BACKGROUND TO THE INVENTION

The immune system possesses the ability to control the homeostasis between the activation and inactivation of lymphocytes through various regulatory mechanisms during and after an immune response. Among these are mechanisms that specifically inhibit and/or turn off an immune response. Thus, when an antigen is presented by MHC molecules to the T-cell receptor, the T-cells become properly activated only in the presence of additional co-stimulatory signals. In the absence of these accessory signals there is no lymphocyte activation and either a state of functional inactivation termed anergy or tolerance is induced, or the T-cell is specifically deleted by apoptosis.

One such co-stimulatory signal involves interaction of CD80 on specialised antigen-presenting cells with CD28 on T-cells, and this signal has been demonstrated to be essential for full T-cell activation. (Lenschow et al. (1996) *Annu. Rev. Immunol.*, 14, 233-258). It would therefore be desirable to provide compounds which inhibit this CD80/CD28 interaction.

Our copending international patent application PCT/GB2004/001008 relates to compounds of formula (I) and pharmaceutically or veterinarily acceptable salts, hydrates or solvates thereof:

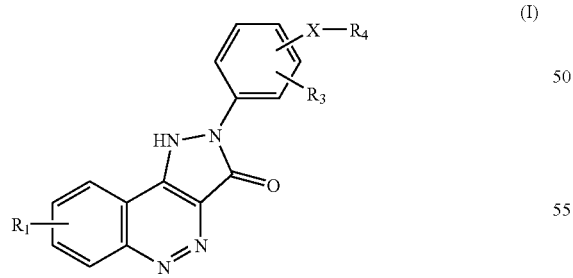

(I)

wherein $R_1$ and $R_3$ independently represent H; F; Cl; Br; —$NO_2$; —CN; $C_1$-$C_6$ alkyl optionally substituted by F or Cl; or $C_1$-$C_6$ alkoxy optionally substituted by F;

$R_4$ represents a carboxylic acid group (—COOH) or an ester thereof, or —C(=O)$NR_6R_7$, —$NR_7$C(=O)$R_6$, —$NR_7$C(=O)$OR_6$, —NHC(=O)$NR_7R_6$ or —NHC(=S)$NR_7R_6$ wherein $R_6$ represents H, or a radical of formula -(Alk)$_m$-Q wherein m is 0 or 1

Alk is an optionally substituted divalent straight or branched $C_1$-$C_{12}$ alkylene, or $C_2$-$C_{12}$ alkenylene, or $C_2$-$C_{12}$ alkynylene radical or a divalent $C_3$-$C_{12}$ carbocyclic radical, any of which radicals may contain one or more —O—, —S— or —N($R_8$)— links wherein $R_8$ represents H or $C_1$-$C_4$ alkyl, $C_3$-$C_4$ alkenyl, $C_3$-$C_4$ alkynyl, or $C_3$-$C_6$ cycloalkyl, and Q represents H; —$NR_9R_{10}$ wherein $R_9$ and $R_{10}$ independently represents H; $C_1$-$C_4$ alkyl; $C_3$-$C_4$ alkenyl; $C_3$-$C_4$ alkynyl; $C_3$-$C_6$ cycloalkyl; an ester group; an optionally substituted carbocyclic or heterocyclic group; or $R_9$ and $R_{10}$ form a ring when taken together with the nitrogen to which they are attached, which ring is optionally substituted; and $R_7$ represents H or $C_1$-$C_6$ alkyl; or when taken together with the atom or atoms to which they are attached $R_6$ and $R_7$ form an optionally substituted monocyclic heterocyclic ring having 5, 6 or 7 ring atoms; and X represents a bond or a divalent radical of formula —(Z)$_n$-(Alk)- or -(Alk)-(Z)$_n$— wherein Z represents —O—, —S— or —NH—, Alk is as defined in relation to $R_6$ and n is 0 or 1.

DESCRIPTION OF THE INVENTION

The present invention relates to a specific compound falling within the general formula (I) of the above-mentioned PCT/GB2004/001008, The invention provides the compound N-(1-aza-bicyclo[2.2.2]oct-3-yl)-4-(6,9-difluoro-3-oxo-1,3-dihydro-pyrazolo[4,3-c]cinnolin-2-yl)-benzamide of formula (IA):

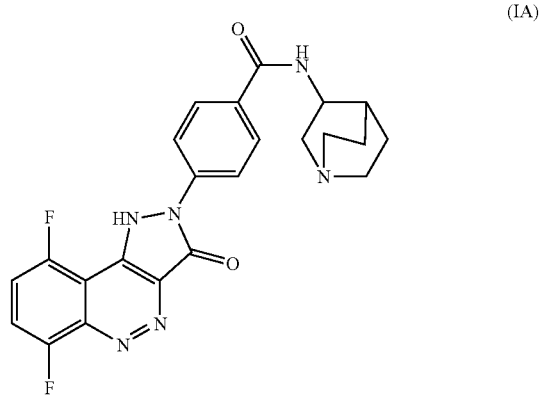

(IA)

and salts, hydrates and solvates thereof.

The carbon atom of the 1-aza-bicyclo[2.2.2]oct-3-yl ring system linked to the benzamido nitrogen is asymmetric, and thus the compound of the invention exists as (R)- or (S)-enantiomers or as an (RS)-enantiomeric mixture. In structure (IA) and elsewhere herein, the bond between that carbon and the benzamido nitrogen is shown in undefined orientation. Both enantiomers (and of course the mixture) have CD80 antagoinist activity, but the (R) enantiomer is currently preferred. The invention therefore includes the compound in the form of the (R)-enantiomer, as well as the (S)-enantiomer, and (RS)-enantiomeric mixtures.

Compound (IA) may exist in the form of tautomers, such as (IB) and (IC):

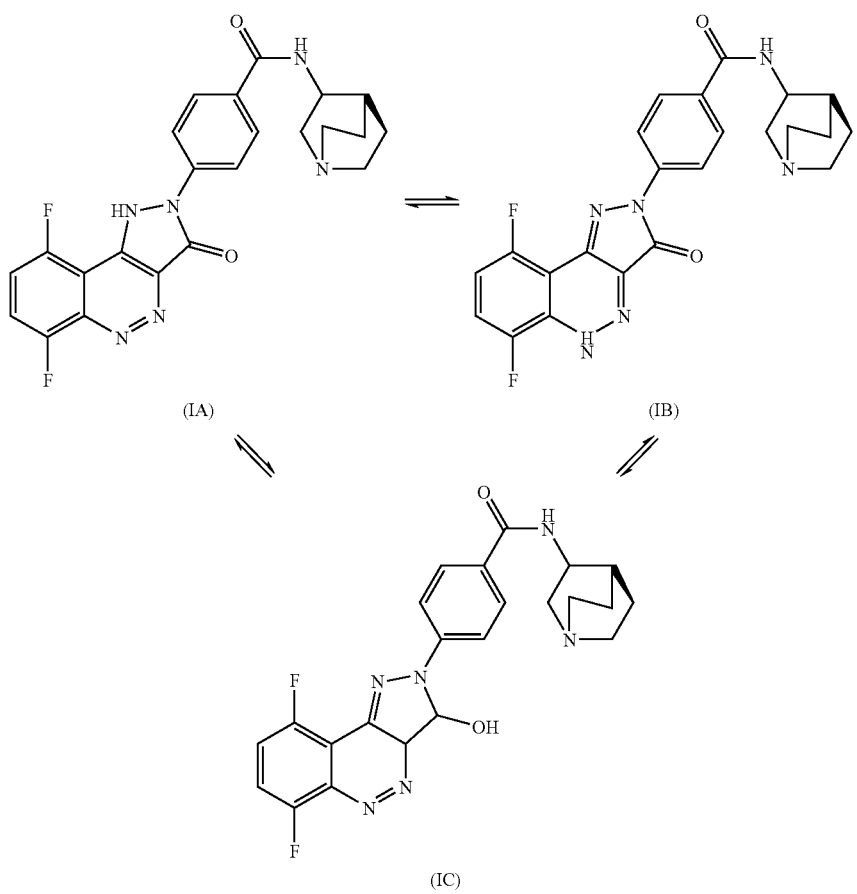

(IA)  (IB)  (IC)

The invention includes all tautomeric forms of N-(1-aza-bicyclo[2.2.2]oct-3-yl)-4-(6,9-difluoro-3-oxo-1,3-dihydro-pyrazolo[4,3-c]cinnolin-2-yl)-benzamide, including in particular those of formulae (IA), (IB), and (IC).

The compound of the invention is a CD80 antagonist. It inhibits the interaction between CD80 and CD28 and thus the activation of T cells, thereby modulating the immune response.

Accordingly the invention also includes:
(i) N-(1-aza-bicyclo[2.2.2]oct-3-yl)-4-(6,9-difluoro-3-oxo-1,3-dihydro-pyrazolo[4,3-c]cinnolin-2-yl)-benzamide, or a pharmaceutically or veterinarily acceptable salt, hydrate or solvate thereof, for use in the treatment of conditions which benefit from immunomodulation, and in particular for immuno-inhibition.
(ii) the use of N-(1-aza-bicyclo[2.2.2]oct-3-yl)-4-(6,9-difluoro-3-oxo-1,3-dihydro-pyrazolo[4,3-c]cinnolin-2-yl)-benzamide or a pharmaceutically or veterinarily acceptable salt, hydrate or solvate thereof in the manufacture of a medicament for the treatment of conditions which benefit from immunomodulation, and in particular for immuno-inhibition.
(iii) a method of immunomodulation, and in particular immuno-inhibition, in mammals, including humans, comprising administration to a mammal in need of such treatment an immunomodulatory effective dose of N-(1-aza-bicyclo[2.2.2]oct-3-yl)-4-(6,9-difluoro-3-oxo-1,3-dihydro-pyrazolo[4,3-c]cinnolin-2-yl)-benzamide or a pharmaceutically or veterinarily acceptable salt, hydrate or solvate thereof.
(iv) a pharmaceutical or veterinary composition comprising N-(1-aza-bicyclo[2.2.2]oct-3-yl)-4-(6,9-difluoro-3-oxo-1,3-dihydro-pyrazolo[4,3-c]cinnolin-2-yl)-benzamide or a pharmaceutically or veterinarily acceptable salt, hydrate or solvate thereof, together with a pharmaceutically or veterinarily acceptable excipient or carrier.

Conditions which benefit from immunomodulation include:
Acute disseminated encephalomyelitis
Adrenal insufficiency
Allergic angiitis and granulomatosis
Amylodosis
Ankylosing spondylitis
Asthma
Autoimmune Addison's disease
Autoimmune alopecia
Autoimmune chronic active hepatitis
Autoimmune haemolytic anaemia
Autoimmune Neutrogena
Autoimmune thrombocytopenic purpura
Behçet's disease
Cerebellar degeneration
Chronic active hepatitis
Chronic inflammatory demyelinating polyradiculoneuropathy
Chronic neuropathy with monoclonal gammopathy
Classic polyarteritis nodosa
Congenital adrenal hyperplasia
Cryopathies
Dermatitis herpetiformis Diabetes
Eaton-Lambert myasthenic syndrome
Encephalomyelitis
Epidermolysis bullosa acquisita
Erythema nodosa
Gluten-sensitive enteropathy
Goodpasture's syndrome
Guillain-Barre syndrome
Hashimoto's thyroiditis
Hyperthyroidism
Idiopathic hemachromatosis
Idiopathic membranous glomerulonephritis
Isolated vasculitis of the central nervous system
Kawasaki's disease
Minimal change renal disease
Miscellaneous vasculitides
Mixed connective tissue disease
Multifocal motor neuropathy with conduction block
Multiple sclerosis
Myasthenia gravis
Opsoclonus-myoclonus syndrome
Pemphigoid
Pemphigus
pernicious anaemia
Polymyositis/dermatomyositis
Post-infective arthritides
Primary biliary sclerosis
Psoriasis
Reactive arthritides
Reiter's disease
Retinopathy
Rheumatoid arthritis
Sclerosing cholangitis
Sjögren's syndrome
Stiff-man syndrome
Subacute thyroiditis
Systemic lupus erythematosis
Systemic necrotizing vasculitides
Systemic sclerosis (scleroderma)
Takayasu's arteritis
Temporal arteritis
Thromboangiitis obliterans
Type I and type II autoimmune polyglandular syndrome
Ulcerative colitis
Uveitis
Wegener's granulomatosis Salts of N-(1-aza-bicyclo[2.2.2]oct-3-yl)-4-(6,9-difluoro-3-oxo-1,3-dihydro-pyrazolo[4,3-c]cinnolin-2-yl)-benzamide include physiologically acceptable acid addition salts and base salts. Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

As mentioned above, the invention includes pharmaceutical or veterinary composition comprising the compound of the invention together with a pharmaceutically or veterinarily acceptable excipient or carrier. In such compositions, it will be understood that the specific dose level for any particular patient will depend upon a variety of factors including the activity of the specific compound employed, the age, body weight, general health, sex, diet, time of administration, route of administration, rate of excretion, drug combination and the cause and severity of the particular disease undergoing therapy. Typical single dose ranges are from 10 mg to 1000 mg. Optimum dose levels and frequency of dosing will be determined by clinical trial.

The compound may be prepared for administration by any route consistent with its pharmacokinetic properties. Orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The drug may also be formulated for administration as a nasal or inhalation spray, or for inhalation as a powder.

The following Example describes the preparation of the compound of the invention by one convenient route. Other routes to the compound are available, using standard literature chemistry, and via routes described in PCT/GB2004/001008.

EXAMPLE

Preparation of (R)—N-(1-Aza-bicyclo[2.2.2]oct-3-yl)-4-(6,9-difluoro-3-oxo-1,3-dihydro-pyrazolo[4,3-c]cinnolin-2-yl)-benzamide A round bottom flask fitted with a reflux condenser, magnetic stirrer and gas bubbler was charged with 4-(6,9-Difluoro-3-oxo-1,3-dihydro-pyrazolo[4,3-c]cinnolin-2-yl)-benzoic acid (300 mg). Thionyl chloride (5 ml) was added and the obtained red suspension was heated to reflux under nitrogen atmosphere. Upon heating gas evolution was observed. After 2 h reflux the clear red solution was cooled to room temperature and excess thionyl chloride removed under vacuum. The mixture was evaporated to dryness to give a red powder.

The powder was suspended in diethylether (20 ml). The (R)-(+)-3-aminoquinuclidine dihydrochloride (174 mg) was mixed with diethylether (10 ml) and ethyl-diisopropyl-amine (0.566 g, 0.762 ml) and added to the acid chloride suspension. [Note: Use of the (S) form of 3-aminoquinuclidine dihydrochloride results in the preparation of the (S)-enantiomer of the desired compound]. The resulting mixture was stirred at room temperature under nitrogen atmosphere. After 4 days stirring product peak [M+H]+451 detectable, as well as carboxylic acid starting material.

The reaction mixture was quenched with water (50 ml) and the solids were collected by filtration and washed with water. The solids were triturated with saturated sodium bicarbonate solution, filtered and washed with water. The product was then purified by HPLC to give the amide.

MS: MH+=451.2

NMR (d6 DMSO, 500 MHz) 1.74 (m, 1H); 1.92 (m, 2H); 2.14 (m, 1H); 2.22 (m, 1H); 2.54 (s, 1H); 3.24 (m, 4H); 3.70 (t, 1H); 4.32 (m, 1H); 7.42 (dt, 1H); 7.60 (m, 1H); 7.99 (d, 2H); 8.36 (d, 2H); 8.58 (d, 1H); 9.58 (brs, 1H).

The compound was tested in the BIAcore and homogeneous time resolved fluorescence (TR-Fret) Assays described below. The results were as follows:

BIAcore: $K_D$=0.35 nM

TR-Fret: $EC_{50}$=0.82 nM

BIAcore Biomolecular Interaction Assay

Biotinylated human CD80 (hCD80-BT) is a recombinant soluble form of a membrane bound receptor molecule (CD80) which binds to CD28 to initiate T cell activation. The interaction between CD80 and CD28 has been extensively investigated (Collins et al, 2002). Biotinylated human HLA-A2-tax is the recombinant soluble form of a membrane bound receptor molecule used as a control protein, and is not expected to interact with the compound.

The BIAcore S51™ system was used for screening the compounds of Examples 1-4 above. A series S sensor chip CM5 was docked onto the BIAcore S51™. Streptavidin was coupled to the carboxymethyl surface using standard amine coupling. The chip surface was activated with 0.2M EDC/0.05M NHS, followed by binding of streptavidin (0.25 mg/ml in 10 mM sodium acetate pH 5.0) and saturation of unoccupied sites with 1 M ethylenediamine.

The BIAcore S51 sensor chip has two separate sensor spots for immobilisation of proteins. hCD80-BT was immobilised on the streptavidin-coated surface of one sensor spot until a response of approximately 3000 RU was observed. A protein to control for non-specific binding of the compound was immobilised on a second sensor spot. The control protein used for these experiments was a biotinylated, soluble form of the human HLA protein.

Dilution series of the compound (1000 nM-0.05 nM) were prepared in running buffer (10 mM, pH 7.4, 150 mM NaCl, 0.005% P20; 5% DMSO).

BIAcore S51™ was run at a flow rate of 30 µl/min using running buffer. Compounds and DMSO standard solutions for correction of data for solvent effects were injected. Data were recorded automatically and were analysed using BIAcore S51 Evaluation software.

REFERENCES

Collins A V et al. (2002) Immunity 17, 201-210 "The interaction properties of costimulatory molecules revisited"

Homogenous Time Resolved Fluorescence Assay

The compound was tested in a cell free homogenous time resolved fluorescence (HT-Fret) assay to determine their activity as an inhibitor of the CD80-CD28 interaction.

In the assay, europium and allophycocyanin (APC) are associated with CD28 and CD80 indirectly (through antibody linkers) to form a complex, which brings the europium and APC into close proximity to generate a signal. The complex comprises the following six proteins: fluorescent label 1, linker antibody 1, CD28 fusion protein, CD80 fusion protein, linker antibody 2, and fluorescent label 2. The table below describes these reagents in greater detail.

| | |
|---|---|
| Fluorescent label 1 | Anti-Rabbit IgG labelled with Europium (1 µg/ml) |
| Linker antibody 1 | Rabbit IgG specific for mouse Fc fragment (3 µg/ml) |
| CD28 fusion protein | CD28-mouse Fc fragment fusion protein (0.48 µg/ml) |
| CD80 fusion protein | CD80 mouse Fab fragment (C215) fusion protein (1.9 µg/ml) |
| Linker antibody 2 | GαMκ-biotin: biotinylated goat IgG specific for mouse kappa chain (2 µg/ml) |
| Fluorescent label 2 | SA-APC: streptavidin labelled allophycocyanin (8 µg/ml) |

On formation of the complex, europium and APC are brought into proximity and a signal is generated.

Non-specific interaction was measured by substituting a mouse Fab fragment (C215) for the CD80 mouse Fab fragment fusion protein (1.9 µg/ml). The assay was carried out in black 384 well plates in a final volume of 30 µl. Assay buffer: 50 mM Tris-HCl, 150 mM NaCl pH7.8, containing 0.1% BSA (w/v) added just prior to use.

Compounds were added to the above reagents in a concentration series ranging between 100 µM-1.7 nM. The reaction was incubated for 4 hours at room temperature. Dual measurements were made using a Wallac Victor 1420 Multilabel Counter. First measurement: excitation 340 nm, emission 665 nm, delay 50 µs, window time 200 µs. second measurement: excitation 340 nm, emission 615 nm, delay 50 µs, window time 200 µs. Counts were automatically corrected for fluorescence crossover, quenching and background.

The invention claimed is:

1. N-(1-Aza-bicyclo[2.2.2]oct-3-yl)-4-(6,9-difluoro-3-oxo-1,3-dihydro-pyrazolo[4,3-c]cinnolin-2-yl)-benzamide or a salt thereof.

2. A compound as claimed in claim 1 in the form of the (R)-enantiomer.

3. A pharmaceutical or veterinary composition comprising N-(1-Aza-bicyclo[2.2.2]oct-3-yl)-4-(6,9-difluoro-3-oxo-1,3-dihydro-pyrazolo[4,3-c]cinnolin-2-yl)-benzamide or a salt thereof together with a pharmaceutically or veterinarily acceptable excipient or carrier.

4. A pharmaceutical or veterinary composition according to claim 3 comprising N-(1-Aza-bicyclo[2.2.2]oct-3-yl)-4-(6,9-difluoro-3-oxo-1,3-dihydro-pyrazolo[4,3-c]cinnolin-2-yl)-benzamide or a salt thereof in an amount to treat conditions which benefit from immunomodulation.

* * * * *